United States Patent
Trittler

(10) Patent No.: US 8,039,640 B2
(45) Date of Patent: Oct. 18, 2011

(54) MORPHINE COMPOUNDS FOR PHARMACEUTICAL COMPOSITIONS

(75) Inventor: Rainer Trittler, Freiburg (DE)

(73) Assignee: Universitätsklinikum Freiburg (DE)

( * ) Notice: Subject to any disclaimer, the term of this patent is extended or adjusted under 35 U.S.C. 154(b) by 561 days.

(21) Appl. No.: 12/278,959

(22) PCT Filed: Feb. 15, 2007

(86) PCT No.: PCT/EP2007/001316
§ 371 (c)(1), (2), (4) Date: Aug. 8, 2008

(87) PCT Pub. No.: WO2007/098860
PCT Pub. Date: Sep. 7, 2007

(65) Prior Publication Data
US 2009/0012110 A1    Jan. 8, 2009

(30) Foreign Application Priority Data
Mar. 2, 2006 (EP) ..................... 06004218

(51) Int. Cl.
*C07D 231/00* (2006.01)
(52) U.S. Cl. ............... 548/364.4; 548/369.4; 548/371.4
(58) Field of Classification Search ............... 548/364.4, 548/369.4, 371.4
See application file for complete search history.

(56) References Cited

FOREIGN PATENT DOCUMENTS
WO    WO 02/098427 A2    12/2002

OTHER PUBLICATIONS

Excerpt from *Natural Products*, "Alkaloids" (1997), p. 166, referencing Goerlitzer, K et al., "Mannich-Bases if Morphine, Isomorphines, and Chloromorphides", Sci. Pharm., vol. 64 (1/4): pp. 391-398 (1996).
International Search Report issued by the European Patent Office for PCT/EP2007/001316 (May 25, 2007).
Hernandez-Delgadillo, G. P. et al. 2002. "Metamizol Potentiates Morphine Nociception But Not Constipation After Chronic Treatment." *European Journal of Pharmacology*. Zusammenfassung. vol. 441, pp. 177-183.

*Primary Examiner* — Karlheinz R Skowronek
*Assistant Examiner* — Sean Basquill
(74) *Attorney, Agent, or Firm* — Chalin Smith; Smith Patent Consulting

(57) ABSTRACT

The invention relates to new morphine compounds of the formula:

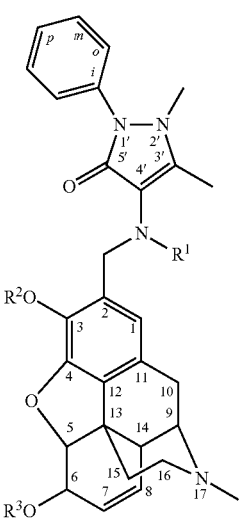

Figure 1:
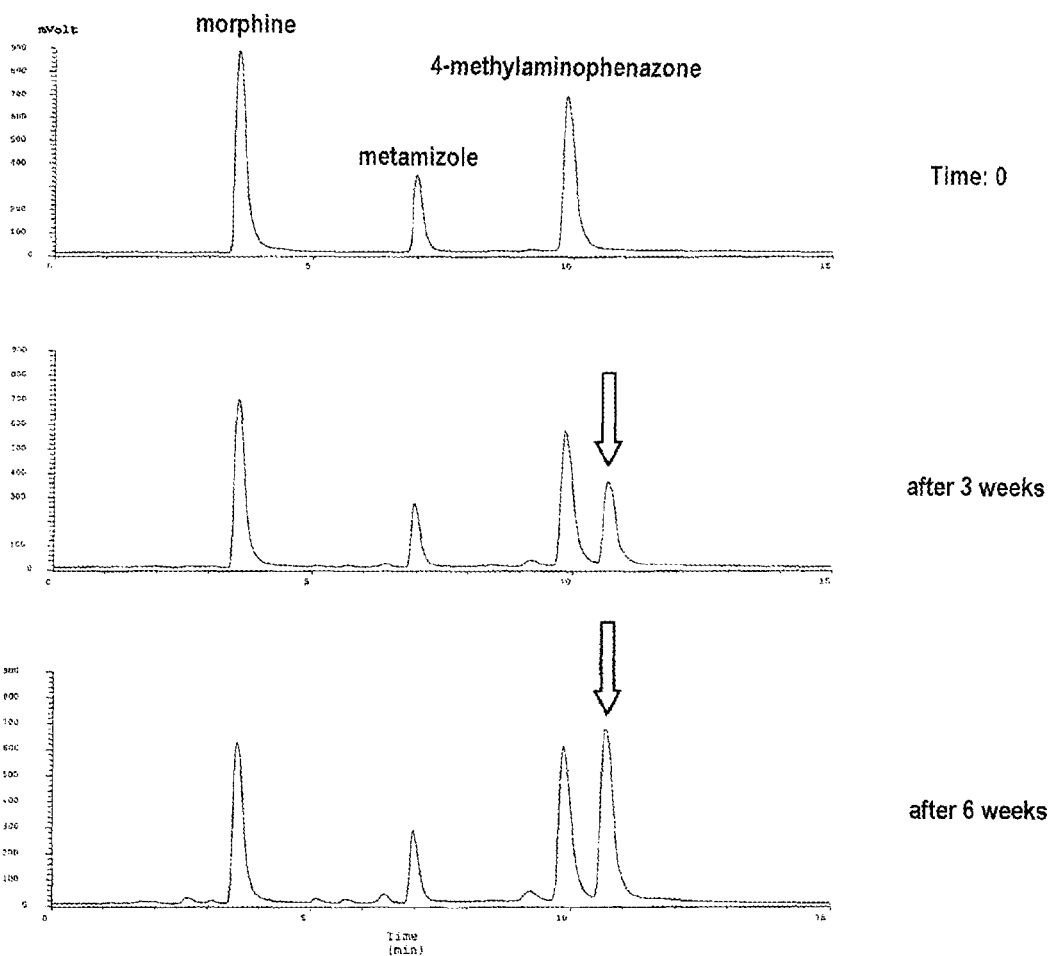

where $R^1$ represents a $C_{1-6}$ alkyl radical and the radicals $R^2$ and $R^3$ are independently selected from the group consisting of hydrogen atoms, methyl groups and acetyl groups.

10 Claims, 3 Drawing Sheets

Chromatograms of the mixture of 18.4 mg/ml morphine sulfate (from MSI® 200) with 40 mg/ml metamizole (from Novalgine® ampoules) in 0.9 % NaCl (storage at 37°C).

Extracted ion chromatograms of the educts and the new substance (EIC 515) from the LC-MS analysis of the mixture of 18.4 mg/ml morphine sulfate (from MSI® 200) with 40 mg/ml metamizole (from Novalgine® ampoules) after storage at 37°C for 6 weeks.

Mass spectrum for the metamorphine compound (formula VI) in comparison with a simulated spectrum for $C_{30}H_{34}N_4O_4$.

MORPHINE COMPOUNDS FOR PHARMACEUTICAL COMPOSITIONS

This application corresponds to the national phase of PCT Application No. PCT/EP2007/001316, filed Feb. 15, 2007, which, in turn, claims priority to European Patent Application No. 06.004218.1, filed Mar. 2, 2006, the contents of both of which are incorporated by reference herein in their entirety.

The invention relates to new morphine compounds of formula I which can be produced from reaction mixtures containing morphine derivatives and pyrazole derivatives, such as metamizole. The invention also relates to pharmaceutical compositions containing the compounds of formula I.

As a pyrazole derivative, metamizole belongs to the group of phenazones and is an analgesic having an antipyretic effect. The analgesic effect is come about by the attenuation of the central pain perception due to an activation of neurons in the pain-inhibitory system. Likewise morphine derivatives are used as opioid analgesics in pain treatment.

The stability of metamizole, N-methyl-N-(2,3-dimethyl-5-oxo-1-phenyl-3-pyrazolin-4-yl)aminomethanesulfonic acid, and the pharmaceutically safe salts thereof depends on the pH. In the neutral and basic environments, metamizole and the pharmaceutically safe salts thereof are stable. In the acidic environment, however, there is a rapid hydrolysis which manifests itself by yellowing.

EP 1 150 660 discloses the production of effervescent tablets containing metamizole, an acceptable stability of the active substance being achieved in spite of the acidic pH of the effervescent formulation.

A problem of morphine derivatives in pain treatment is the potential danger of addiction caused by some compounds. The very fast passing of the blood-brain barrier can cause the patients' addiction to these substances. With respect to the side-effect of morphine, U.S. Pat. No. 5,521,178 describes the use of flupirtine as an analgesic preparation without any addiction potential. The use of pro-drugs which slowly form a morphine derivative might also contribute to the reduction of the addiction potential.

Morphine alkaloids can also be used as quaternary nitrogen compounds. The production of these compounds is described in WO 2004/043964, for example.

The production of medicaments containing the active substance metamizole in combination with other active substances or ingredients is limited because of the stability problem of metamizole. A drug composition which contains metamizole and morphine, for example, does not yet exist.

It has been possible to show by way of experiment that under suitable conditions, such as suitable pH and reaction temperature, morphine derivatives having pyrazole derivatives, in particular metamizole, enter into reactions so as to form new morphine compounds. The products of these reactions are the subject matter of the present invention.

No reaction occurs under respective conditions. Thus, no new morphine compounds could be detected in a mixture of morphine and metamizole when stored at room temperature for 2 weeks.

It is an object of the present invention to provide these new compounds for pharmaceutical compositions. Compounds of formula I can be used e.g. as a pro-drug in pain treatment, for example. An advantage may be that a pharmaceutical composition can be provided which contains morphine derivatives together with pyrazole derivatives as active substances in the form of a pro drug, this pharmaceutical composition remaining stable even on prolonged storage and containing a constant quantity ratio of the active substances.

Another advantage of the new morphine compounds can also be a retard effect on account of pharmacokinetic or pharmacodynamic effects.

A reduction of the side-effects with respect to the active substances morphine and metamizole might also be an advantageous property of the new compounds since e.g. the distribution of the active substances over the compartments of the human body will differ.

In addition, the compounds according to the invention might have a new pharmacodynamic effect at the morphine receptor.

A pharmaceutical composition can also contain salts, e.g. in the form of quaternary N-derivatives of compounds of formula I.

The present invention thus relates to compounds of formula I

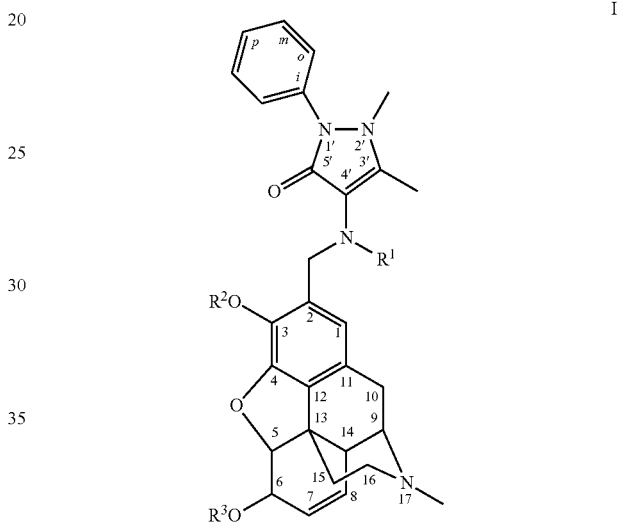

where $R^1$ represents a $C_{1-6}$ alkyl radical, such as the methyl, ethyl, propyl or butyl radical, and radicals $R^2$ and $R^3$ are independently selected from the group consisting of hydrogen atoms, methyl and acetyl groups.

Compounds of formula I are preferred, where $R^1$ represents a methyl group and radicals $R^2$ and $R^3$ are independently selected from the group consisting of hydrogen atoms, methyl and acetyl groups.

Particularly preferred are compounds of formula I, where $R^1$ represents a methyl group and radicals $R^2$ and $R^3$ represent the same radicals and are selected from the group consisting of hydrogen atoms, methyl and acetyl groups.

The invention also relates to compounds of formula I, where $R^1$ represents a methyl group and radicals $R^2$ and $R^3$ represent hydrogen atoms.

The present invention also concerns a pharmaceutical composition which comprises one or several compounds of formula I or salts of these compounds, where other additives and/or active substances may additionally be contained. Conventional, pharmaceutically acceptable compounds are in consideration as salts.

A pharmaceutical composition is preferred which comprises a compound of formula I or a salt of this compound, where $R^1$ is a methyl group and radicals $R^2$ and $R^3$ are hydrogen atoms.

More preferred are pharmaceutical compositions, where the compound of formula I is contained in a quantity of substance of at least 20% by weight, preferably at least 50% by weight and most preferably at least 90% by weight, based on the total composition.

The invention also relates to the use of a compound of formula I for the production of an infusion solution, where radicals $R^1$, $R^2$ and $R^3$ are as defined above.

Particularly preferred is the use of a compound of formula I for the production of a pharmaceutical composition for treating pain, where radicals $R^1$, $R^2$ and $R^3$ are as defined above.

Moreover, the invention relates to a process for the production of compounds of formula I

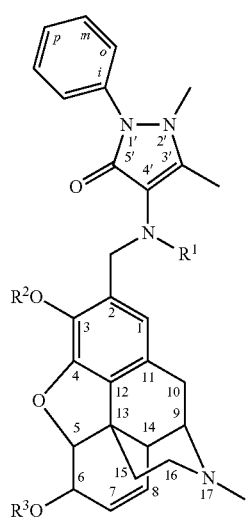

where a compound of formula II or a salt thereof

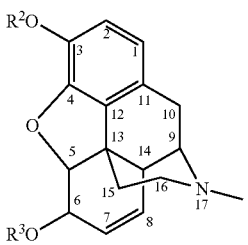

and a compound of formula III or a salt thereof

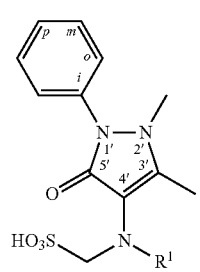

are reacted and where $R^1$ represents a $C_{1-6}$ alkyl radical and radicals $R^2$ and $R^3$ are independently selected from the group consisting of hydrogen atoms, methyl and acetyl groups.

Preferred is the process where $R^1$ represents a methyl group and radicals $R^2$ and $R^3$ represent hydrogen atoms.

Regarding the synthesis of the compounds of formula I it is preferred to use compounds of formulae II and III as starting substances. Compounds of formula II are referred to as morphine derivatives. The compound of formula II is referred to as morphine if both radicals $R^2$ and $R^3$ are hydrogen atoms and as codeine if radical $R^2$ is a hydrogen atom and $R^3$ is a methyl group and as heroin if $R^2$ and $R^3$ are acetyl groups. A preferred compound of formula II is morphine.

Compounds of formula III are pyrazole derivatives or derivatives of N-methyl-N-(2-methyl-5-oxo)-1-phenyl-3-pyrazolin-4-yl)aminomethanesulfonic acid, where in the 3 position of the pyrazoline ring (radical $R^1$) a $C_{1-6}$ alkyl radical is found which contains 1 to 6 carbon atoms. Particularly preferred is a methyl group in the 3 position ($R^1$=methyl); the corresponding compound is referred to as metamizole.

The compounds of formula I are produced by mixing the compounds of formula II and III or the salts thereof, followed by storage at a temperature which is above 37° C. (without light protection, at a reaction time of about 6 weeks), preferably it is 45° C., more preferably 65° C. and most preferably 80° C.

$R^1$ is here a $C_{1-6}$ alkyl radical and radicals $R^2$ and $R^3$ are independently selected from the group consisting of hydrogen atoms, methyl and acetyl groups. A solvent suitable for the reaction can be an aqueous solution, for example. The pH of the reaction mixture must be less than 6.0 when the reaction starts, preferably the pH is less than or equal to 5.7 and most preferably it is less than 5.0. The pH can be adjusted according to methods known to a person skilled in the art in this connection. The end of the reaction can be determined e.g. by liquid chromatography coupled with mass spectroscopy (LC-MS, liquid chromatography with mass spectroscopy) and is reached when the desired conversion is determined. The reaction mixture can be processed by common methods. The subsequent purification of the reaction mixture and isolation of the new morphine compounds can be done by high performance liquid chromatography (HPLC) methods or also by column chromatography. The products can also be identified and isolated by mass spectroscopy (LC-MS) and NMR spectroscopy.

In another production process of the compounds of formula I, the synthesis is carried out in water or an organic solvent. Here, $R^1$ represents a $C_{1-6}$ alkyl radical and radicals $R^2$ and $R^3$ are independently selected from the group consisting of hydrogen atoms, methyl and acetyl groups. The pH of the reaction mixture must be less than 6.0 when the reaction starts; the pH is preferably less than or equal to 5.7 and most preferably it is less than 5.0. The pH can be adjusted according to the methods known to the person skilled in the art for this purpose. The reaction temperature is greater than 37° C., preferably it is 45° C., more preferably 65° C. and most preferably 80° C. The end of the reaction can be determined by mass spectroscopy (LC-MS), for example, and is reached when the desired conversion is determined. The reaction mixture can be processed by common methods. The subsequent separation of the reaction mixture and isolation of the new morphine compounds can be made by HPLC methods or also by column chromatography. The products can also be identified and isolated by LC-MS and NMR (nuclear magnetic resonance) spectroscopy.

A third production process uses as starting compounds morphine derivatives of formula II, formaldehyde and compounds of formula IV. The reaction conditions, the processing of the reaction mixtures and the purification of the products follow from the two other methods.

The formation of the compounds of formula I can be explained in terms of chemistry as follows: Under acidic conditions, compounds of formula III can be decomposed thereby forming formaldehyde. For example, metamizole ($R^1$ is a methyl group) decomposes into 4-methylaminophenazone (formula IV).

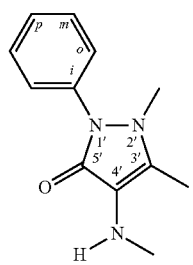

IV

This is followed by a Mannich reaction of the morphine derivatives (formula II) as CH-acidic component with formaldehyde and the compounds of formula IV. The Mannich reaction of morphine as CH-acidic component with formaldehyde and other amines (e.g. diethylamine) was described earlier by Görlitzer and Weltrowski (*Beiträge zur Chemie and Analytik von Morphin* [articles on the chemistry and analysis of morphine], special print from studies of Braunschweigsche Wissenschaftliche Gesellschaft, J. Cramer Verlag Braunschweig, 2002). This reaction mechanism is further supported by the drug incompatibility of methenamine and phenanzone discovered by Eger, Troschütz and Roth. A Mannich reaction also proceeds here under mild conditions (Eger K, Troschütz R, Roth H: Arzneistoffanalyse [drug analysis], 4$^{th}$ edition, page 293, Deutscher Apothekerverlag Stuttgart 1999).

When a freshly prepared mixture of morphine derivatives with e.g. metamizole is administered, no reaction to compounds of formula I has to be expected in relevant amounts in the human body. On the one hand, the formaldehyde necessary for this is very quickly metabolized by the human body and is no longer available for the Mannich reaction. On the other hand, the residence time of the substances in the body is short as compared to a reaction time of several weeks so that no relevant amount of compound of formula I can form.

In a particularly preferred embodiment of the invention, metamizole (formula IV) and morphine (formula V) are used as starting compounds.

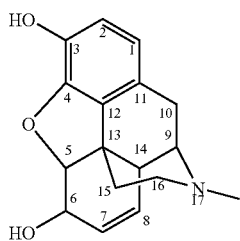

V

When a metamizole mixture is reacted with morphine, the compound of formula VI forms when there is a slightly acidic pH ($R^1$ is a methyl group, radicals $R^2$ and $R^3$ are hydrogen atoms), which is referred to below as "metamorphine".

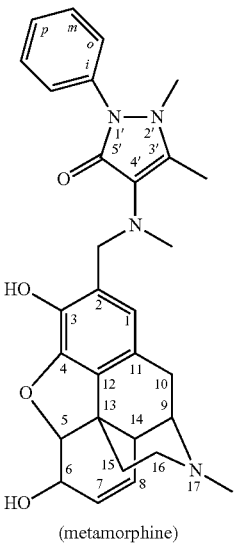

VI (metamorphine)

Another embodiment of the invention relates to a pharmaceutical composition which contains one or several compounds of formula I, where $R^1$ represents a $C_{1-6}$ alkyl radical and radicals $R^2$ and $R^3$ are independently selected from the group consisting of hydrogen atoms, methyl and acetyl groups. The compound of formula I is produced according to one of the above described methods but is not limited to these methods. The pharmaceutical composition can also be a mixture of a compound of formula I or the salt thereof with compounds of formulae II and III (or the salts thereof) or the degradation/hydrolysis products thereof which can be used for the synthesis of the compound of formula I. These pharmaceutical compounds preferably contain the compounds of formula I in a substance amount of at least 20% of the active substances, particularly preferably they contain at least 40%, more preferably they contain at least 50%, most preferably at least 80% by weight, based on the total weight of the composition. The pharmaceutical composition according to the invention can contain further active substances or preferably only active substances of formula I. The pharmaceutical composition can be administered intravenously or subcutaneously as an infusion or injection solution but also in any other form of application such as tablets, suppositories or drops orally or rectally.

Another embodiment contains the compound metamorphine of formula VI ($R^1$ is a methyl group, radicals $R^2$ and $R^3$ are hydrogen atoms) in the pharmaceutical composition. The compound of formula VI is preferably produced according to one of the above described methods, however it is not limited to these methods. Such a composition can contain further active substances and ingredients. These pharmaceutical compositions preferably contain the compound of formula VI in a substance amount of at least 20% of active substances, particularly preferably they contain at least 40%, more preferably they contain at least 50%, most preferably at least 80%, based on the total weight of the composition. The pharmaceutical composition can be administered intravenously or subcutaneously in form of an infusion or injection solution but also in any other form of application, such as tablets, suppositories or drops, orally or rectally.

The below examples serve for explaining the invention.

EXAMPLE 1 a) Synthesis

An infusion bag was filled with a mixture of 18.4 mg/ml morphine sulfate (from MSI® 200) and 40 mg/ml metamizole (from Novalgine® ampoules) in 0.9% NaCl and then stored in an incubator at 37° C. (without light protection). The new substance "metamorphine" formed after 6 weeks in a yield of about 50% (based on the starting morphine content). See in this connection also the chromatograms shown in FIG. 1.

b) Analysis with HPLC

Samples were taken from the infusion bag directly after the production and after 3 and 6 weeks and were frozen at −30° C. directly afterwards. For the purpose of analysis, the samples were thawed and separated by means of the below described methods using HPLC directly afterwards. All starting substances and also the new substance "metamorphine" were fully separated by this method. FIG. 1 shows chromatograms of the mixture stored at 37° C. of 18.4 mg/ml morphine sulfate (from MSI® 200) and 40 mg/ml metamizole (from Novalgine® ampoules) in 0.9% NaCl as a function of the reaction time.
Devices:
   HPLC pump K-1001 (Knauer, Autosampler SL 10AD VP (Shimadzu), column furnace CTO-10AS VP (Shimadzu), diode array detector K-2700 (Knauer)
Column:
   Merck Purospher STAR, RP 18e, 125×4 mm
Gradient:

| | | |
|---|---|---|
| 0 min | 95% phosphate buffer pH 5 | 5% acetonitrile |
| 10 min | 70% phosphate buffer pH 5 | 30% acetonitrile |
| 10.01 min | 95% phosphate buffer pH 5 | 5% acetonitrile |

Flow: 1 ml/min c) Analysis with LC-MS

The HPLC method was transferred to LC-MS (esquire 3000, Bruker Daltronics) and the mass of the new compound was determined.
Column:
   Merck Purospher STAR, RP 18e, 125×4 mm
Gradient:

| | | |
|---|---|---|
| 0 min | 95% ammonium phosphate buffer pH 5 | 5% actonitrile |
| 20 min | 70% ammonium phosphate buffer pH 5 | 30% acetonitrile |
| 20.01 min | 95% ammonium phosphate buffer pH 5 | 5% acetonitrile |

Flow: 0.5 ml/min, concluded after 30 min

Figure 2:
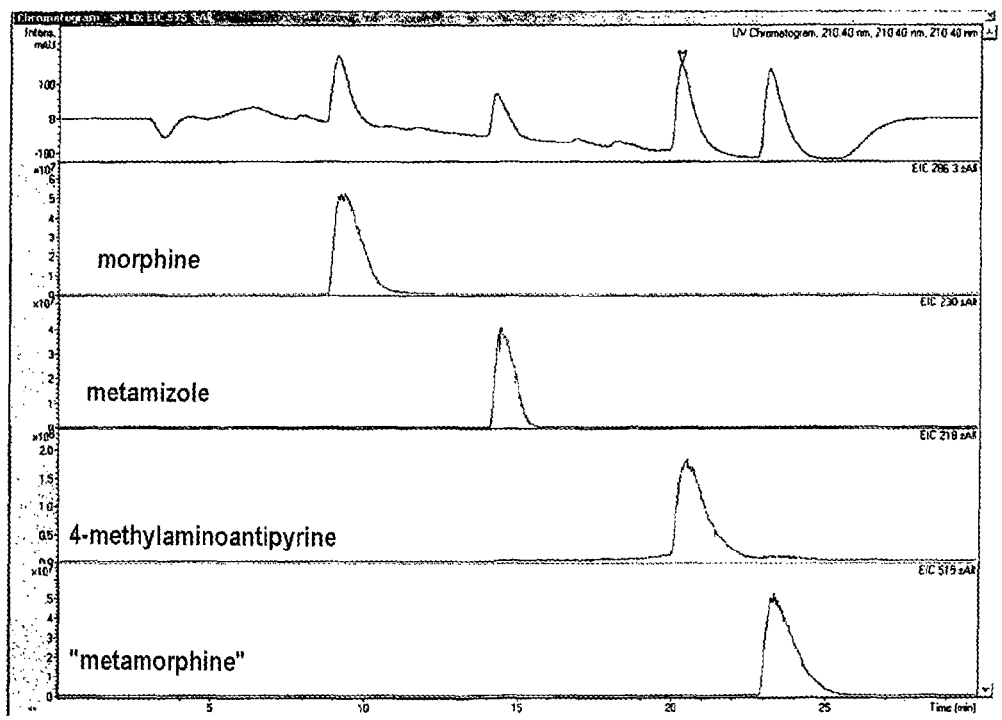

MS Conditions:
   ESI (electron impact ionization) was used in the positive mode (Trap Drive 36.2, Octopol RF Amplitude 149.8 Vpp, Lens 2-60 volt, Capillary Exit 112.4 volt, dry temp. 250° C., nebulizer 30.0 psi, dry gas 12.00 l/min, HV capillary 4000 V, HV end plate offset −500 V). The settings in the ion trap were: rolling on, rolling averages 2 cts, scan begin 50 m/z, scan end 1000 m/z, averages 5 spectra, max. accu time 200000 µs, ICC target 40000, charge control on. FIG. 2 shows the extracted ion chromatograms of the educts and the new substance. For a better comparability, the U.V. chromatogram is also exhibited.

Figure 3:
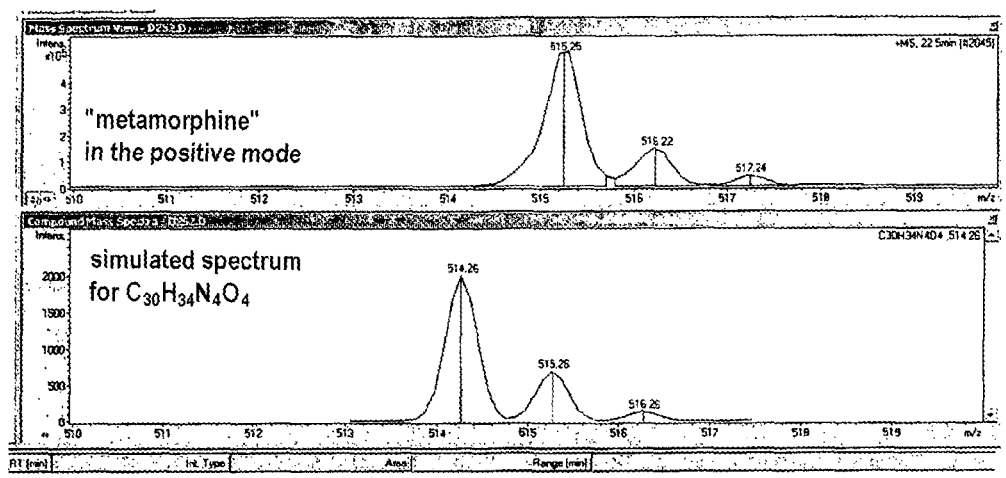

Since the measurement was made in the positive mode, the mass of the new substance is lighter by one proton, i.e. 514 m/z. The mass spectrum of the substance is well in conformity with a simulated mass spectrum of a compound having empirical formula $C_{30}H_{34}N_4O_4$, see FIG. 3.

d) Isolation of the Product

The isolation was carried out on an Agilent LC-MS apparatus with mass detector model SL G1946G with splitter G1968D and a fraction collector G1364A. The samples were injected by means of an Agilent autosampler G1313A (injection volume 1800 µl).
Column:
   Zorbax SB-C18, 9.4×150 mm, 5 µm
Gradient:

| | | |
|---|---|---|
| 0 min | 95% ammonium formate buffer pH 5 | 5% acetonitrile |
| 10 min | 70% ammonium formate buffer pH 5 | 30% acetonitrile |
| 20 min | 70% ammonium formate buffer pH 5 | 30% acetonitrile |
| 20.01 min | 5% ammonium formate buffer pH 5 | 95% acetonitrile |
| 23 min | 5% ammonium formate buffer pH 5 | 95% acetonitrile |
| 23.01 min | 95% ammonium formate buffer pH 5 | 5% acetonitrile |

Flow: 3.5 ml/min, end after 29 min

MS Conditions:
   ESI was used in the positive mode and a mass-based (mass 514, i.e. m/z 515) collection was carried out by means of the splitter (splitting ratio 2900:1). (Dry temp. 300° C., nebulizer, 35.0 psi, dry gas 12.00 l/min, HV capillary 3000 V, fragmentor voltage 100 V).

The collected fraction was vacuum-dried by means of a rotary evaporator and taken up in methanol. The methanol phase was then concentrated again in a new round-bottom flask. About 300 mg of the new substance could be isolated in this way.

e) Characterization of the Product by NMR Experiments

Table 1 shows the results of $^{13}$C-NMR and $^1$H-NMR, the numbering scheme of the compound follows from formula VI.

In addition, NOE (nuclear Overhauser enhancement) signals were measured, in particular between: H-1 and 2-CH$_2$, H-10 (2.81), 4'-NMe (weak); 4'-NMe and 2-CH$_2$, 3'-Me; 3'-Me and 2'-Me and o.

TABLE 1

| Number of the carbon atom | $^{13}$C-NMR (δ, ppm) | $^1$H-NMR (δ, ppm) |
|---|---|---|
| 1 | 122.3 | 6.47 (s) |
| 2 | 127.8 | |
| 3 | 140.4 | |
| 4 | 147.8 | |
| 5 | 92.4 | 4.90 (m) |
| 6 | 67.6 | 4.25 (m) |
| 7 | 135.5 | 5.70 (d, 9.8 Hz) |
| 8 | 126.7 | 5.32 (d, 9.8 Hz) |
| 9 | 61.8 | 4.05 (m) |
| 10 | 23.2 | 2.81 (m) |
| | | 3.20 (m) |

TABLE 1-continued

| Number of the carbon atom | $^{13}$C-NMR ($\delta$, ppm) | $^{1}$H-NMR ($\delta$, ppm) |
|---|---|---|
| 11 | 123.1 | |
| 12 | 130.1 | |
| 13 | 43.3 | |
| 14 | 39.1 | 3.01 (m) |
| 15 | 33.7 | 2.00 (m) |
| | | 2.35 (m) |
| 16 | 47.9 | 3.01 (m) |
| | | 3.24 (m) |
| 17-Me | 41.5* | 2.91 (s) |
| 2-CH$_2$ | 57.6 | 4.12 (s) |
| 4'-NMe | 41.6* | 2.75 (s) |
| 4' | 121.0 | |
| 3' | 152.0 | |
| 3'-Me | 10.6 | 2.03 (s) |
| 2'-Me | 35.8 | 3.01 (s) |
| i | 135.6 | |
| o | 126.5 | 7.35 (d, 7.4 Hz) |
| m | 130.5 | 7.50 (t, 7.9 Hz) |
| p | 128.9 | 7.39 (t, 7.5 Hz) |

*or vice versa.

The invention claimed is:

1. A compound of formula I:

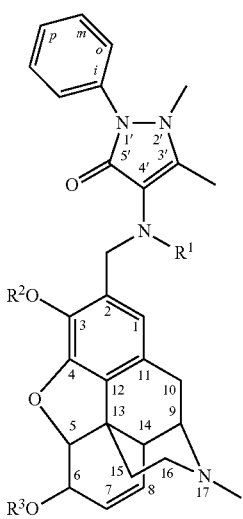

I where R$^1$ represents a C$_{1-6}$ alkyl radical and radicals R$^2$ and R$^3$ are independently selected from the group consisting of hydrogen atoms, methyl and acetyl groups.

2. The compound according to claim 1, wherein R$^1$ represents a methyl group and the radicals R$^2$ and R$^3$ are independently selected from the group consisting of hydrogen atoms, methyl and acetyl groups.

3. The compound according to claim 1, wherein R$^1$ represents a methyl group and the radicals R$^2$ and R$^3$ represent the same radicals and are selected from the group consisting of hydrogen atoms, methyl and acetyl groups.

4. The compound of claim 1, wherein R$^1$ represents a methyl group and the radicals R$^2$ and R$^3$ represent hydrogen atoms.

5. A pharmaceutical composition which comprises one or several compounds of formula I of claim 1 or salts of these compounds, wherein additives and/or other active substances may additionally be included.

6. The pharmaceutical composition according to claim 5, which comprises a compound of formula I or a salt of this compound, wherein R$^1$ represents a methyl group and radicals R$^2$ and R$^3$ represent hydrogen atoms.

7. The pharmaceutical composition according to claim 5, wherein the compound of formula I is contained in a substance amount of at least 20% of the active substances.

8. An infusion solution comprising a compound of formula I of claim 1, wherein the radicals R$^2$ and R$^3$ are as defined in claim 1.

9. A method of producing compounds of formula I:

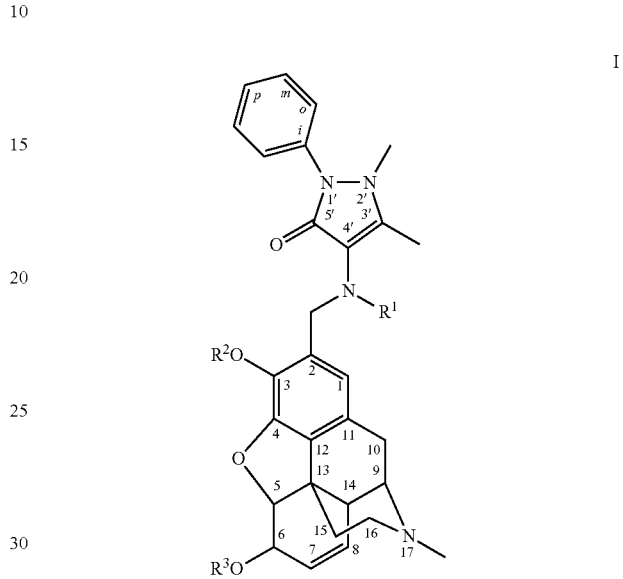

I using a compound of formula II or a salt thereof

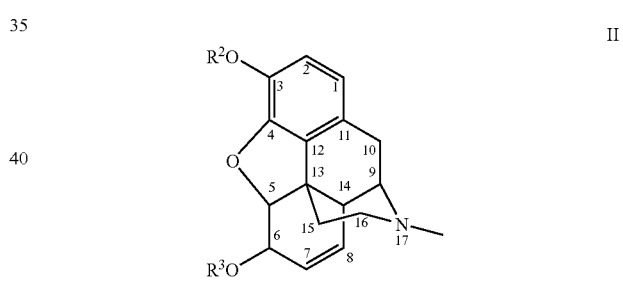

II and a compound of formula III or a salt thereof

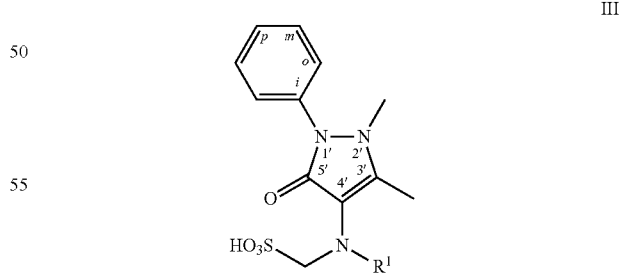

III wherein R$^1$ represents a C$_{1-6}$ alkyl radical and radicals R$^2$ and R$^3$ are independently selected from the group consisting of hydrogen atoms, methyl and acetyl groups.

10. The method according to claim 9, wherein R$^1$ represents a methyl group and the radicals R$^2$ and R$^3$ represent hydrogen atoms.

* * * * *